US011883302B2

United States Patent
Dunkley et al.

(10) Patent No.: US 11,883,302 B2
(45) Date of Patent: Jan. 30, 2024

(54) SPINAL IMPLANT HAVING A COMPRESSIBLE INSERT

(71) Applicant: Warsaw Orthopedic, Inc., Warsaw, IN (US)

(72) Inventors: Ian Dunkley, Irvine, CA (US); Jerbrena C. Jacobs, Hernando, MS (US); Jason A. Rister, Memphis, TN (US); Dawin A. Rodriguez Santiago, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 80 days.

(21) Appl. No.: 17/532,366

(22) Filed: Nov. 22, 2021

(65) Prior Publication Data

US 2023/0157841 A1 May 25, 2023

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/3008* (2013.01); *A61F 2002/30069* (2013.01); *A61F 2002/30092* (2013.01); *A61F 2002/3093* (2013.01); *A61F 2002/30326* (2013.01); *A61F 2002/30772* (2013.01); *A61F 2310/00359* (2013.01)

(58) Field of Classification Search
CPC .. A61F 2/447; A61F 2/44; A61F 2/442; A61F 2/30771; A61F 2002/30069; A61F 2002/3008; A61F 2002/30092; A61F 2002/30326; A61F 2002/30772; A61F 2002/3093; A61F 2310/00359

USPC ........................................... 623/17.11–17.16
See application file for complete search history.

(56) References Cited

U.S. PATENT DOCUMENTS

| 4,678,470 | A |  | 7/1987 | Nashef et al. |
| 4,759,766 | A | * | 7/1988 | Buettner-Janz ....... A61F 2/4425 623/17.15 |
| 4,789,663 | A |  | 12/1988 | Wallace et al. |
| 4,888,366 | A |  | 12/1989 | Chu et al. |
| 5,231,169 | A |  | 7/1993 | Constantz et al. |
| 5,626,861 | A |  | 5/1997 | Laurencin et al. |

(Continued)

FOREIGN PATENT DOCUMENTS

| CN | 203815664 U | 9/2014 |
| DE | 202021000221 U1 | 2/2021 |

(Continued)

OTHER PUBLICATIONS

International Searching Authority, European Patent Office, Munich, Germany, International Search Report and Written Opinion of the International Searching Authority, Application No. PCT/US22/48592.

*Primary Examiner* — Jessica Weiss
(74) *Attorney, Agent, or Firm* — Sorell, Lenna & Schmidt, LLP (57) ABSTRACT

A spinal implant for insertion into and positioning in an intervertebral space is provided. The insert comprises a compressible support configured to change the height of the insert, wherein the insert comprises a first portion having a first surface and a compressible support adjacent to the first surface; and a second portion having a second surface and a second compressible support adjacent to the second surface. A method for fusing two adjacent vertebrae utilizing the spinal implant including the bone insert is also provided.

19 Claims, 7 Drawing Sheets

(56) References Cited

U.S. PATENT DOCUMENTS

| | | | |
|---|---|---|---|
| 6,059,829 A * | 5/2000 | Schlapfer | A61F 2/4455 606/247 |
| 7,056,341 B2 * | 6/2006 | Crozet | A61B 17/86 623/17.11 |
| 7,147,665 B1 * | 12/2006 | Bryan | A61F 2/4425 623/17.16 |
| 7,563,455 B2 | 7/2009 | McKay | |
| 7,601,174 B2 * | 10/2009 | Kelly | A61B 17/1757 623/17.13 |
| 7,799,076 B2 | 9/2010 | Sybert et al. | |
| 7,837,740 B2 | 11/2010 | Semler et al. | |
| 7,935,121 B2 | 5/2011 | Lidgren et al. | |
| 8,758,791 B2 | 6/2014 | McKay | |
| 8,802,652 B2 | 8/2014 | Myntti et al. | |
| 9,585,764 B2 | 3/2017 | McKay | |
| 9,693,866 B2 | 7/2017 | Temple et al. | |
| 11,173,043 B1 * | 11/2021 | Robbins | A61F 2/4455 |
| 2002/0123750 A1 * | 9/2002 | Eisermann | A61F 2/441 606/76 |
| 2002/0183848 A1 * | 12/2002 | Ray | A61F 2/441 623/17.12 |
| 2012/0191189 A1 | 7/2012 | Huang | |
| 2013/0297029 A1 * | 11/2013 | Kana | A61F 2/4455 623/17.16 |
| 2017/0333204 A1 * | 11/2017 | Huang | A61F 2/447 |
| 2019/0274838 A1 | 9/2019 | Manwill et al. | |

FOREIGN PATENT DOCUMENTS

| | | |
|---|---|---|
| JP | 2003169845 A | 6/2003 |
| WO | 2003047645 A1 | 6/2003 |

\* cited by examiner

SPINAL IMPLANT HAVING A COMPRESSIBLE INSERT

BACKGROUND

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions and ailments may lead to damage of the spine, intervertebral discs and/or the vertebral members. The damage may result from a variety of causes including, but not limited to, events such as trauma, a degenerative condition, a tumor, or infection. Damage to the intervertebral discs and vertebral members can lead to pain, neurological deficit, and/or loss of motion of the spinal elements.

Various procedures include replacing a section of or an entire intervertebral disc, a section of or an entire vertebral member, or both. One or more spinal implants may be inserted to replace damaged discs and/or vertebral members. The implants are configured to be inserted into an intervertebral space and contact against adjacent vertebral members. The implants are intended to reduce or eliminate the pain and neurological deficit and increase the range of motion.

The curvature of the spine and general shapes of the vertebral members may make it difficult for the implants to adequately contact the adjacent vertebral members or to position the adjacent vertebral members in a desired orientation. There is a need for spinal implants or devices configurable to match the spinal anatomy for secure contact and/or desired orientation of the spinal implants or devices implanted into an intervertebral disc space.

In the spinal surgery field, surgical procedures are often performed to correct problems with displaced, damaged or degenerated intervertebral discs due to trauma, disease or aging. Bone graft materials are often used in spine fusion surgery. Current spinal fusion implants utilize grafts of either bone or artificial implants to fill the intervertebral disc space.

In particular, one method of treating a damaged disc is by immobilizing the area around the injured portion and fusing the immobilized portion by promoting bone growth between the immobilized spine portions. This often requires implantation of a spinal implant to provide the desired spacing between adjacent vertebrae to maintain foraminal height and decompression. That is, a spinal implant may be inserted into the intervertebral disc space of two neighboring vertebral bodies or into the space created by removal of damaged portions of the spine.

Formed spinal implants are used to treat damaged vertebral discs. However, these formed spinal implants are only available in limited sizes and shapes and provide little ability for customization. These formed spinal implants also may not conform to cavities in the vertebral disc, which may make implantation of the implants at the target tissue site more challenging.

While generally effective, the use of bone grafts has some limitations. Autologous bone grafts, being obtained from the patient, require additional surgery and present increased risks associated with its harvesting, such as risk of infection, blood loss and compromised structural integrity at the donor site. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, the use of bone grafts is generally limited by the available shapes and sizes of grafts provided.

As to bone grafts, allograft bone is a reasonable bone graft substitute for autologous bone. It is readily available from cadavers and avoids the surgical complications and patient morbidity associated with harvesting autologous bone. Human allograft tissue is widely used in orthopedic surgery.

Xenograft bone is also another bone graft substitute where bone from one species is used in another species. The bone can be treated in order to reduce rejection by, for example, crosslinking, sintering, or use of supercritical carbon dioxide.

Indeed, allograft is a preferred material by surgeons for conducting interbody fusions because it will remodel over time into host bone within the fusion mass. However, though allograft tissue has certain advantages over the other treatments, allograft is typically available in only limited size ranges, thus making it difficult to provide spinal implants, in particular, interbody implants in a preferred geometrical shape having an adjustable height. It would be desirable to construct a spinal implant having a compressible insert that can expand or contract to the specific anatomic area that it is being inserted into. It would be beneficial to provide a spinal implant that has a compressible insert that can be implanted into an intervertebral disc space and adapt to the anatomic region of the spine. It would also be beneficial to have a spinal implant that has a compressible insert that can also receive bone material.

SUMMARY

The present disclosure fills the foregoing needs by providing a spinal implant having a compressible insert that can expand or contract to the specific anatomic area that it is being inserted into. In some embodiments, the spinal implant that has a compressible insert can also receive bone material (e.g., allograft bone, demineralized bone matrix (DBM), ceramic material, etc.).

In one embodiment, there is a spinal implant for positioning between adjacent vertebrae, the spinal implant comprising a first contact surface and a second contact surface, the first contact surface and the second contact surface configured to contact adjacent vertebrae, the spinal implant also comprising a gap configured to receive an insert, the insert configured to have a compressible height such that in a compressed state, the height of the insert is shorter than a height of the spinal implant and in an expanded state, the height of the insert is configured to extend beyond a height of the first contact surface and a height of the second contact surface, the insert also having a first portion and a second portion, the first portion comprising a first surface and a compressible support adjacent to the first surface and the second portion having a second surface and a second compressible support adjacent to the second surface of the insert.

In another embodiment, there is a spinal implant for the transforaminal interbody fusion of lumbar vertebral column segments, the spinal implant comprising a main body having a first surface and a second surface situated opposite the first surface, the first surface and the second surface configured to contact the vertebral column segments, the main body also having an inner perimeter, a filling hole, and an engagement part, the engagement part having a recess configured to allow a portion of a positioning instrument to position the spinal implant between vertebral column segments; and an insert disposed in the filling hole, the insert comprising a first portion having a first surface and a compressible support adjacent to the first surface; and a second portion having a second surface and a second compressible support adjacent to the second surface.

In yet another embodiment, there is a method for fusing two adjacent vertebrae, the method comprising placing a spinal implant having at least two ends into an intervertebral space adjacent vertebrae in need of fusion, the spinal implant configured to receive an insert; placing the insert into the spinal implant and compressing the insert into a compressed state, wherein a height of the insert is the same or shorter than a height of the spinal implant, the insert comprising a first portion having a first surface and a compressible support adjacent to the first surface; and a second portion having a second surface and a second compressible support adjacent to the second surface.

While multiple embodiments are disclosed, still other embodiments of the present disclosure will become apparent to those skilled in the art from the following detailed description, which is to be read in connection with the accompanying drawing(s). As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying drawings where:

DEFINITIONS

To aid in the understanding of the disclosure, the following non-limiting definitions are provided:

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized."

"Demineralized bone matrix" or "DBM" as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the disclosure.

"Osteoconductive," as used herein, refers to the ability of a non-osteoinductive substance to serve as a suitable template or substance along which bone may grow. In some embodiments, "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

"Osteogenic," as used herein, refers to the ability of an agent, material, or implant to enhance or accelerate the growth of new bone tissue by one or more mechanisms such as osteogenesis, osteoconduction, and/or osteoinduction. In some embodiments, "osteogenic" refers to the ability of a graft material to produce bone independently. To have direct osteogenic activity, the graft must contain cellular components that directly induce bone formation. For example, a collagen matrix seeded with activated mesenchymal stem cells (MSCs) would have the potential to induce bone formation directly, without recruitment and activation of host MSC populations. Because many osteoconductive scaffolds also have the ability to bind and deliver bioactive molecules, their osteoinductive potential will be greatly enhanced.

"Osteoimplant," as used herein, refers to any bone-derived implant prepared in accordance with the embodiments of this disclosure and therefore is intended to include expressions such as bone membrane, bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive. In some embodiments, "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous extracellular matrix (ECM), which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral content.

The term "allograft" refers to a graft of tissue obtained from a donor of the same species as, but with a different genetic make-up from the recipient, as a tissue transplant between two humans.

The term "autologous" refers to being derived or transferred from the same individual's body, such as for example an autologous bone marrow transplant.

The term "xenograft" refers to tissue or organs from an individual of one species transplanted into or grafted onto an organism of another species, genus, or family.

The term "morbidity" refers to the frequency of the appearance of complications following a surgical procedure or other treatment.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols, which have only a marginal effect on the patient.

The term 'cavity' includes and encompasses voids, apertures, bores, depressions, holes, indentations, grooves, channels, notches or the like. In some embodiments, a plurality of cavities may be provided throughout one or more surfaces of and/or within the implant body and/or the bone insert thus enabling an additional plurality of allograft pieces to be retained in various locations of the spinal implant and the bone insert.

"Shape memory" as used herein, refers to materials that are capable to recover their original shape from a significant and seemingly plastic deformation upon a particular stimulus is applied. This deformation includes a compression that cause a dimension (length, width and/or height) to decrease such that a shape memory effect allows the materials to regain their original length, width or height.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Certain terminology, which may be used in the following description is for convenience only and is not limiting. For example, the words "right", "left", "top" and "bottom" designate directions in the drawings to which reference is made. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Bone allograft is a preferred material by surgeons for conducting interbody fusions because it will remodel over time into host bone within the fusion mass. Polymer compositions for interbody fusion do not allow for direct bone attachment or bonding to further stabilize the implant and fusion mass. In addition, surgical procedures are increasingly moving towards minimally invasive surgical procedures in which smaller interbody implants can be inserted through smaller surgical incisions and expanded once placed in the disc space. The present disclosure overcomes the drawbacks of the prior art by providing various exemplary designs of spinal implants comprising desirable allograft compositions that allow disc distraction and therefore stabilize the spine and increase the height of adjacent vertebrae. The present disclosure also provides implants containing non-bone skeleton structures configured to include cavities including other materials, for example, allograft.

The present disclosure overcomes these drawbacks by providing various exemplary designs of spinal implant having an insert disposed in a hole or gap in the spinal implant or in a filling hole, the insert comprising, consisting essentially of or consisting of a first portion, a middle portion and a second portion. One exemplary configuration, according to the present disclosure, involves the first portion having a first surface, a third surface and a first compressible support disposed between the first surface and the third surface, the second portion having a second surface, a fourth surface and a second compressible support disposed between the second surface and the fourth surface, the middle portion comprises a pillar extending across the height of the middle portion, and projections extending transversely from the pillar.

The compressible support of the insert comprises, consists essentially of, or consists of structures and/or materials that are capable to deform either isotropically or in one direction to achieve a desired height of protruding and/or a filling hole inside a spinal implant. The deformation of the supports are elastic and, in some embodiments, allow packing of bone graft material onto and/or around the bone insert. The plastic deformation is not avoided in this process. The modulus of elasticity of the compressible insert can be calculated from an unconstrained stress curve versus a strain curve when the bone insert is compressed into the spinal implant hole or gap without any surface raised passing the contact surfaces of the implant.

The bone insert is more compressible relative to the spinal implant or the spinal implant body. The spinal implant or the spinal implant body is more rigid relative to the bone insert. The bone insert, in some embodiments, can be made from a material having a modulus of elasticity from about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$. In some embodiments, the materials can be made from polyethylene terephthalate (PET) and has a modulus of elasticity of about $3.15\times10^8$ dynes/cm$^2$. In some embodiments, the deformation also affects the porosity of the bone insert. In some embodiments, the porosity of the bone insert comprises an average diameter size of 1 mm in the original fully expanded state to 10 microns in a compressed state. In some embodiments, the bone insert maintains about 200 microns porosity when inserted into a patient with the spinal implant. In some embodiments, the shape-memory effect of the shape-memory material used in the bone insert allows the bone insert to deform either isotropically or in one direction, such as along a vertical axis, while maintaining the width on a horizontal axis.

In some embodiments, the bone insert comprises 30%-97% by weight of ceramic materials. In some embodiments the bone insert comprises about 30, 35, 40, 45, 50, 55, 60, 65, 70, 75, 80, 85, 90, to about 95% by weight of ceramic materials. In some embodiments, the bone insert comprises 60-80% by weight bone materials, such as for example, ceramic, DBM, or the like.

In some embodiments, the grooves, recesses, projections, serrations or combinations thereof of one or more portions of the bone insert correspond to grooves, recesses, projections, serrations or combinations thereof of the spinal implant allowing the insert to reduce or prevent movement of the insert and allow for spine stabilization and the distance between vertebrae to be increased. In some embodiments, the serrations have shapes comprising triangular, pyramid, cone, spike, keel shapes or combinations thereof.

In some embodiments, the bone insert, in an uncompressed state, can be inserted into a gap or hole of the spinal implant, which allows it to be compressed by the walls of the spinal implant or cannula used to insert it and then the insert can expand from its compressed state back to non-compressed state such that once inserted in the disc space with the spinal implant, the bone insert can expand from the compressed state to contact the bone. The insertion can be done by a minimally invasive procedure.

The spinal implant can be designed for different approaches to the interbody space, such as for example, posterior lumbar interbody fusion (PLIF), transforaminal lumbar interbody fusion (TLIF), anterior lumbar interbody fusion (ALIF) and/or direct lateral interbody fusion (DLIF). The spinal implant provided can be inserted through surgical techniques via open, mini-open, or minimal access spinal technologies or minimally invasive surgical techniques.

In some embodiments, the spinal implant comprises a spinal implant having a gap or hole, a first implant end and a second implant end, the first implant end and the second implant end configured to contact adjacent vertebrae, an insert disposed in the gap of the implant having a height extending beyond the first implant end and the second implant end, the insert comprising a compressible support configured to change the height of the insert, wherein the insert comprising a first portion, a middle portion and a second portion, the first portion having a first surface, a third surface and the compressible support disposed between the first surface and the third surface, the second portion having a second surface, a fourth surface and a second compressible support disposed between the second surface and the fourth surface, the middle portion comprises a pillar extending across the height of the middle portion, and projections extending transversely from the pillar.

In some embodiments, a spinal implant for the transforaminal interbody fusion of lumbar vertebral column segments is provided. The spinal implant comprises a main body, the main body including a first surface and a second surface situated opposite the first surface, surface areas of at least one of the first surface and the second surface which come into direct contact with the vertebral column segments being formed with a dislocation protection, the main body having an inner side wall and an outer side wall situated opposite the inner side wall, and a first end portion and a second end portion situated opposite the first end portion, the main body having formed therein at least one filling hole situated between the inner side wall and the outer side wall; an engagement part, the engagement part being formed at the second end portion, the second end portion of the main body having a access recess formed therein, the access recess configured to allow a portion of a positioning instrument for positioning the implant between vertebral column segments; and an insert disposed in the at least one filling hole, the insert comprising a first portion, a middle portion and a second portion, the first portion having a first surface, a third surface and a first compressible support disposed between the first surface and the third surface, the second portion having a second surface, a fourth surface and a second compressible support disposed between the second surface and the fourth surface, the middle portion comprises a pillar extending across the height of the middle portion, and projections extending transversely from the pillar.

Figure 1:
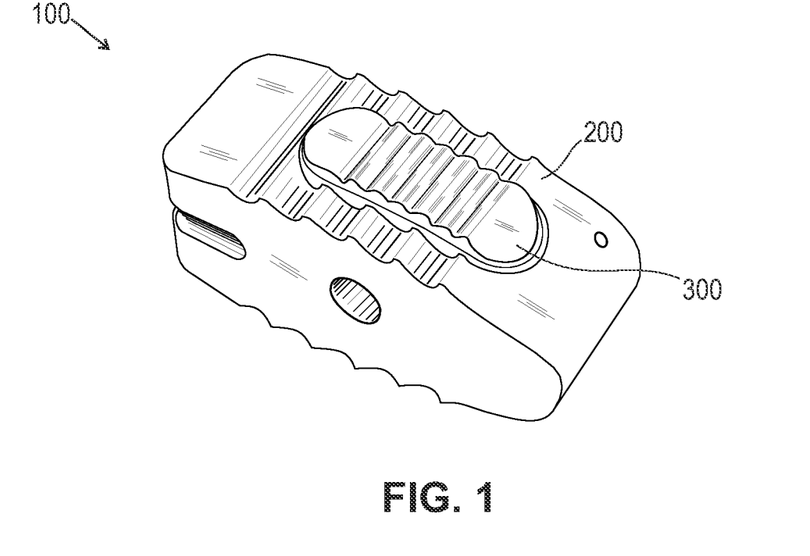
FIG. 1 is a perspective view of an exemplary spinal implant containing an exemplary compressible bone insert according to one embodiment.
Figure 2:
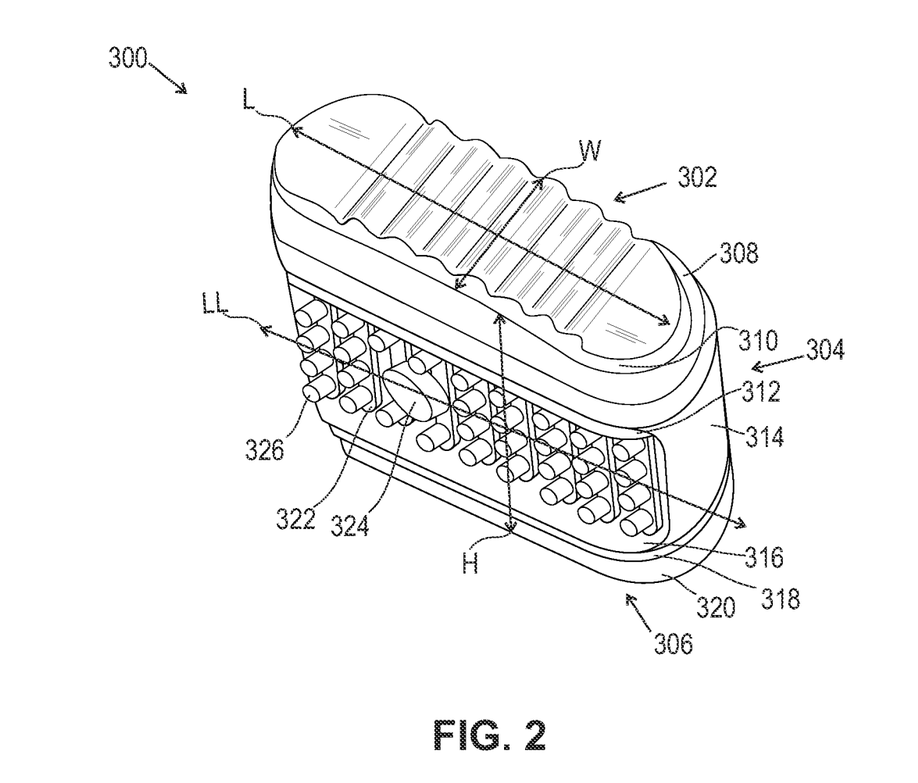
FIG. 2 is a perspective view of an exemplary compressible bone insert according to another embodiment.
Figure 9:
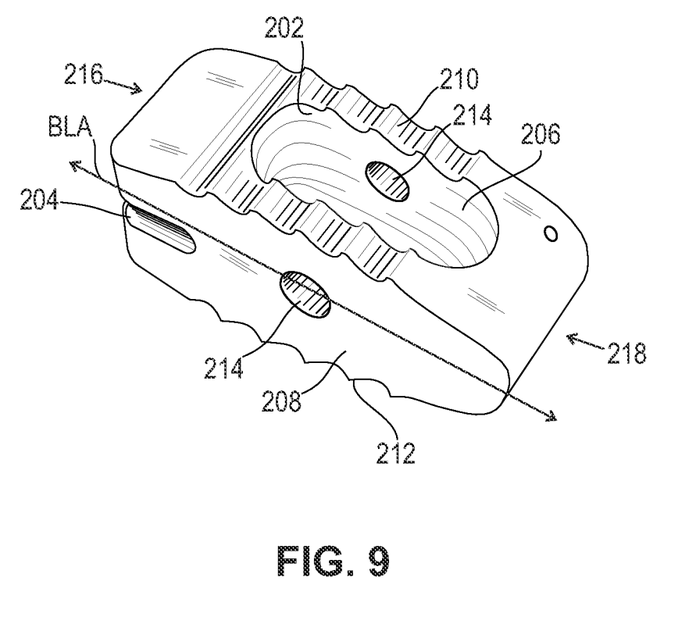
FIG. 9 is a perspective view of a spinal implant device without a compressible bone insert. The spinal implant is shown as an intervertebral or interbody cage.

FIG. 1 depicts an exemplary embodiment of a spinal implant 100 with a bone insert 300 disposed in the spinal implant. The bone insert can provide a spongy characteristic to the bone insert. FIG. 9 depicts the spinal cage (200 in FIG. 1) of a spinal implant without the bone insert disposed in a hole or gap of the spinal implant. The spinal implant comprises an inner perimeter 202 forming a hole 206 or gap configured to receive a bone insert and/or bone grafts. In some embodiments, the hole or gap may be provided in any of a variety of shapes in addition to the generally rectangular/oval shapes including but not limited to generally circular, square, oblong, curved, triangular, rectangular, and other polygonal or non-polygonal shapes.

The insert comprises various shapes corresponding to the shape of the hole or gap promoting fusion between the upper and lower vertebral bodies. The outer perimeter 208 forms a general structure and support for the implant. In some embodiments, the spinal implant comprises an oval, a circular, a rectangular or a sickle shape. In some embodiments, the spinal implant comprises an engagement part 204 configured to receive an instrument to manipulate the position of the implant. In some embodiments, the spinal implant comprises an insertion end 216 disposed adjacent to the engagement part and a non-insertion end 218 opposite the insertion end extending across a longitudinal axis BLA of the spinal implant. The spinal implant also comprises a viewing hole 214 configured to allow a user to confirm the position of the bone insert. In some embodiments, the viewing hole is used to access a block of the insert to physically orient a compressible support by fitting protrusions of the insert. In some embodiments, there is a second viewing hole disposed opposite to the viewing hole. The viewing holes are disposed transversely to the longitudinal axis of the spinal implant.

The spinal implant comprises a first contact surface 210 and a second contact surface 212 configured to come into direct contact with the vertebral column. These contact surfaces have specific structures serving as a dislocation protection. These structures can have, for example, the shape of truncated pyramids or truncated cones, or may be realized in the form of cut, spherical bodies. In some embodiments, the implant is made of a bioelastic synthetic material. In one embodiment, the material of which the implant is made is polyetheretherketone (PEEK). In some embodiments, the implant comprises PEEK, titanium or a combination thereof. In some embodiments, the implant can comprise cortical bone. In some embodiments, the implant includes X-ray markers situated on the main body thereof.

FIGS. 2-5 are various views of an exemplary bone insert that is configured to be disposed in the hole, gap, or filling hole of the spinal implant. The bone insert has length L, width W, height H, first portion 302, middle portion 304, second portion 306. The first portion has a first surface 308 configured to contact the bone. The first portion comprises perimeter 310 configured to engage and contact a perimeter of the filling hole. The perimeter also assists insert to be secured within the filling hole and stabilizes the insert pre-operation, during and post-operation. The middle portion has a first surface 312, a second surface 316 and side support 314 extending across and connecting the first surface and the second surface. The side support 314 extends along the outer most edge of the middle portion and is disposed on the two ends of the length of the insert. In some embodiments, the side support comprises a rectangular band, film, or plane. The middle portion, in some embodiments, comprises pillars or struts 322 extending from the first surface to the second surface. The struts comprise projections 326.

In some embodiments, the projections comprise discs, beads, cylindrical and rectangular shapes or a combination thereof. The projections extend transversely to a longitudinal axis LL of the insert. The projections extend in the width direction and are shorter than the width of the insert. The longitudinal axis runs parallel to the length of the insert.

The middle portion also comprises block 324 disposed in a section of struts. The block comprises various shapes including cylindrical, rectangular or triangular shapes. In some embodiments, the block is a cylindrical structure extending across the width of the insert and is disposed in place of a section of a plurality of struts. The disposition of the block corresponds to a viewing window of the spinal implant. In some embodiments, the block is a solid structure without any hole. In some embodiments, the block allows the orientation of the insert within the implant and prevents migration, ejection, or simply falling out of the insert. In some embodiments, the block has a cavity allowing an instrument to manipulate the insert or spinal implant. In some embodiments, the block has a through-bore allowing an instrument to manipulate the insert or spinal implant. The block also allows a user to observe and ensures that the insert is properly placed inside the spinal implant or in the hole or gap of the implant. The height of the insert extends from the first surface of the first portion to the second surface of the second portion.

Figure 3:
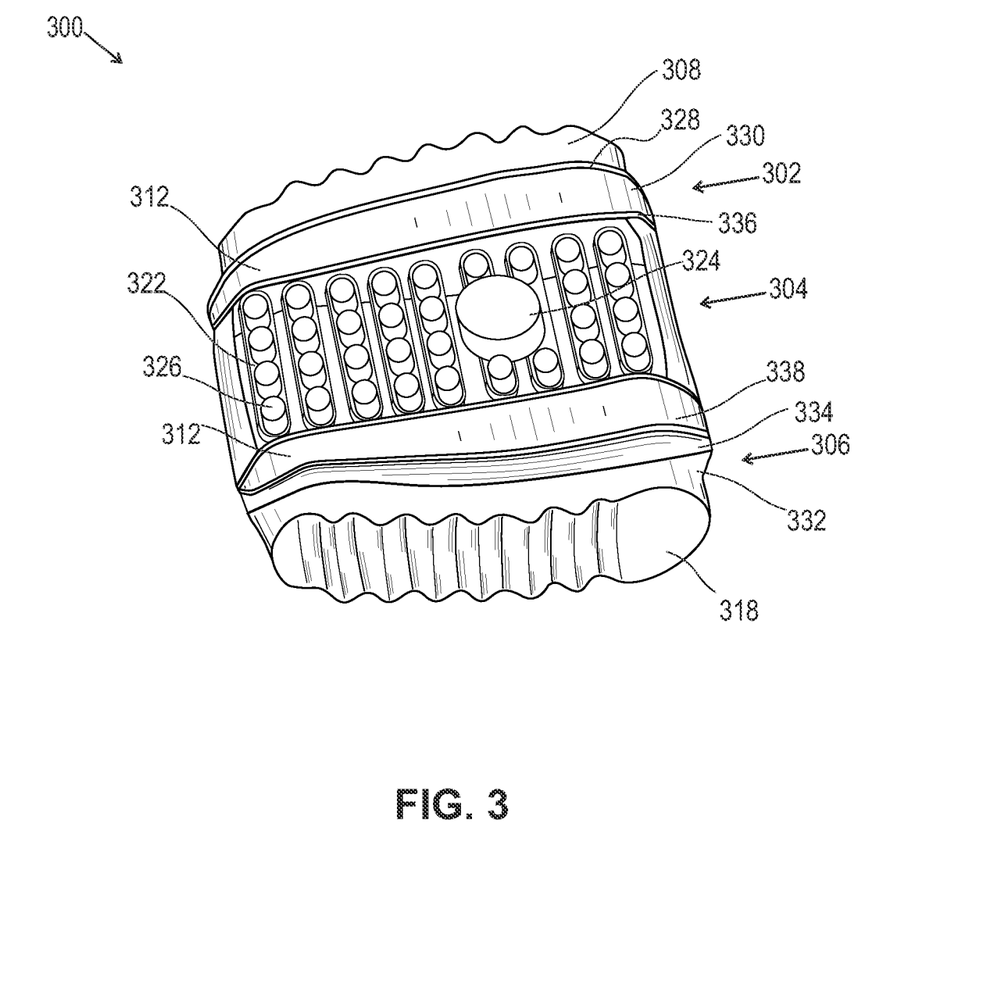
FIG. 3 is a top view of the bone insert as in FIG. 2.
Figure 4:
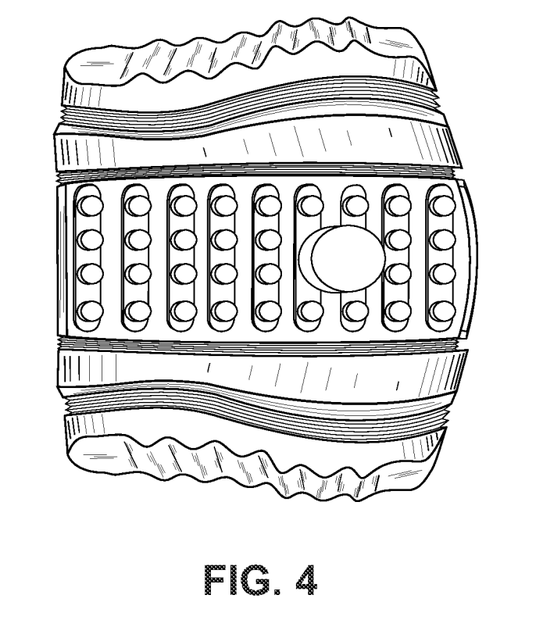
FIG. 4 is a side view of the compressible bone insert as in FIG. 2 according to one embodiment.
Figure 5:
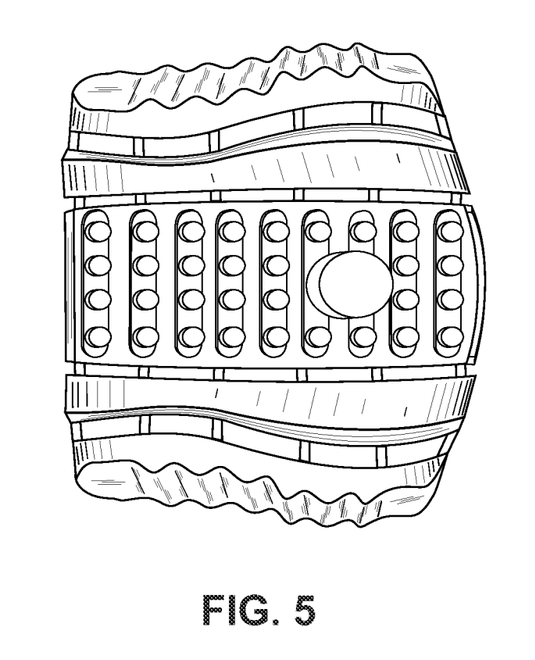
FIG. 5 is a side view of the compressible bone insert as in FIG. 2 according to an alternative embodiment.

As shown in FIGS. 3-5, the first portion further comprises a third surface 330 disposed between the first surface of the first portion and the first surface of the middle portion. The first portion comprises a first support 328 between the first surface and the third surface. The first support comprises a compressible, elastic structure that deforms vertically along the height of the insert while the width of the first support deforms minimally or has no deformation. The specific direction of the deformation allows the insert to be compressed and expand to contact bones following the contour of the bone better without exerting additional frictional forces to the walls of the implant, which may destabilize the insert from the spinal implant. In some embodiments, the first support has a plurality of ridges and grooves forming an accordion-like structure. In some embodiments, the first support has a strut-like structure having a pillar and treads circling around the pillar which acts as a spring and allows the pillar portion to deform vertically with little or no horizontal deformation. In some embodiments, the insert has a third support 336 disposed between the third surface and the first surface of middle portion. In some embodiments, the insert has a fourth support 338 disposed between the fourth surface and the second surface of the middle portion. The first, second, third and fourth supports can have the same or different combinations of the embodiments as discussed above.

The second portion has a second surface 318 configured to contact the bone for fusion. The second portion has a perimeter 320 similar to the perimeter of the first portion and configured to engage and contact a perimeter of the filling hole. The second portion comprises a fourth surface 334 disposed between the second surface of the second portion and the second surface of the middle portion. The second portion comprises a second support 332 between the second surface and the fourth surface. The second support has a similar structure and functions to the first support.

In some embodiments, the insert is configured to impart a vertical compression to the spinal implant. In one embodiment, the insert is an osteoconductive insert. In another embodiment, the insert is monolithic. In some embodiments, the insert is made of a bioelastic synthetic material. In one embodiment, the material of which the insert is made is polyetheretherketone (PEEK). In some embodiments, the insert includes X-ray markers corresponding to the X-ray markers on the spinal implant.

Figure 6:
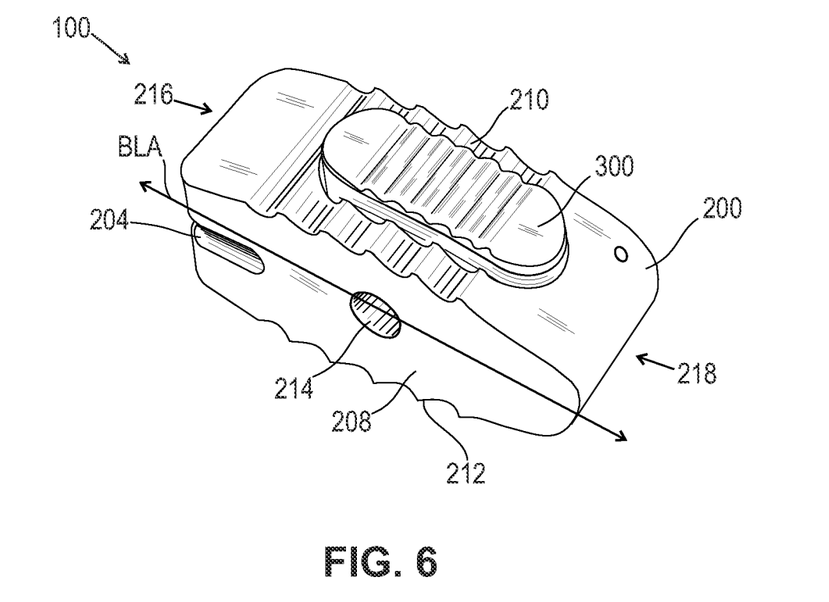
FIG. 6 is a perspective view of a spinal implant containing a compressible bone insert disposed in a hole or gap of the spinal implant where the bone insert is in a non-compressed state.
Figure 7:
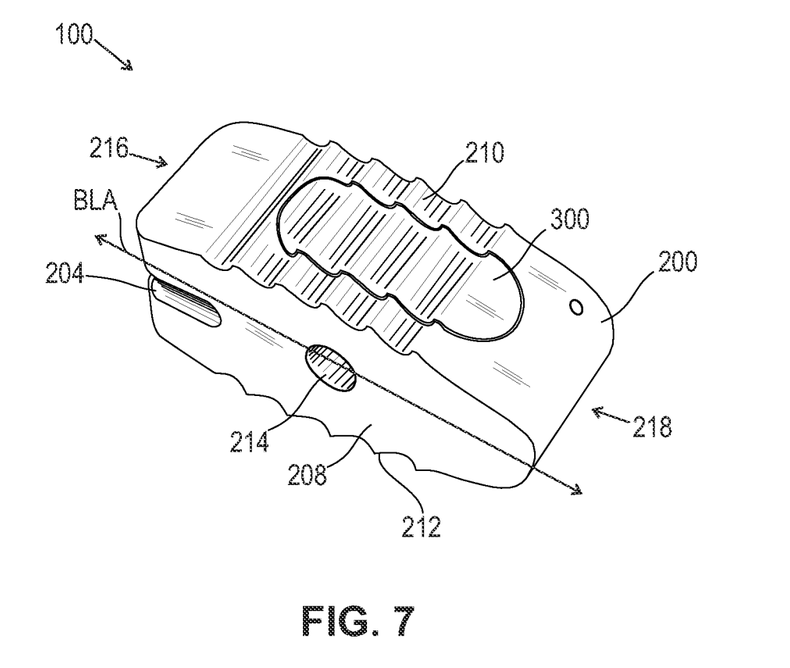
FIG. 7 is a perspective view of a spinal implant device containing a compressible bone insert in a compressed state.
Figure 8:
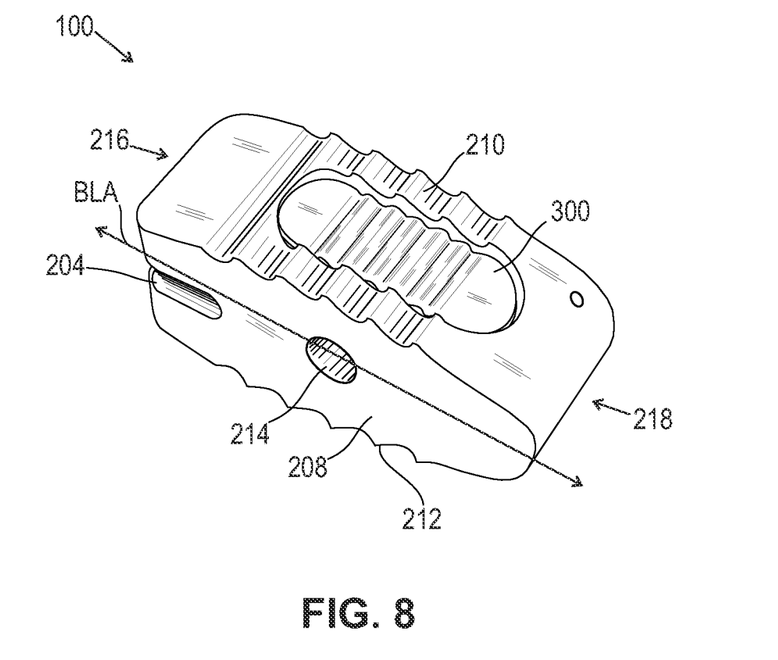
FIG. 8 is a perspective view of a spinal implant device containing a compressible bone insert in a compressed state according to yet another embodiment.

FIGS. 6-8 depict the bone insert in various states inside the hole of the spinal implant. The insert can be fully compressed as to have the entire height of the insert inside the hole, for example, as shown in FIG. 8. This can also be in its fully compressed state when the spinal implant is inserted into the spine. In some embodiments, the insert can expand to have a highest point of contact surface including the first surface of the first portion and the second surface of the second portion to match with a highest point of the implant's first and second contact surfaces, while other parts of the surface of the insert can be higher than the implant. In other words, the contour of the first surface of the insert does not match the contour of the contact surface of the implant completely. In some embodiments, the insert can expand to have entire contact surfaces, the first surface of the first portion and the second surface of the second portion, flush with and/or correspond to the entire first and second contact surfaces of the implant such that the contour of the first surface of the insert corresponds to the contour of the first contact surface of the spinal implant. In some embodiments, the insert can expand partially such that a portion of the contact surface may expand more than another portion of the contact surface when different resistances are exerted to the contact surface. In some embodiments, the insert can be fully expanded as to have the entire contact surface raised beyond the contact surfaces of the implant (e.g., as shown in FIG. 6). In some embodiments, the insert's capability to be compressible then expandable is due to its shape-memory materials. The shape-memory materials used to make the insert allows the insert to regain its length, width and/or height after compression. In some embodiments, the insert also regains some or all of its porosity after compression. The insert is more elastic and compressible relative to the other portions of the spinal implant. For example, the insert is more elastic and compressible relative to the spinal cage.

Advantageously, the spinal implant and the bone insert may be formed via machining into any size or shape to accommodate the desired application and/or delivery conditions. The spinal implant and the bone insert may further be configured to include any desired features, such as cavities, projections, etc. in any desired location or orientation, as discussed above.

In some embodiments, the spinal implant may comprise an allograft portion that is configured to be joined to another allograft portion. In this way, the interbody device can be joined before it is implanted at or near the target site. The spinal implant can have mating surfaces comprising recesses and/or projections and reciprocating recesses and/or projections (e.g., joints) that allow the implant to be assembled before implantation. Assembly can also include, for example, use of an adhesive material to join parts of the implant together and provide strong interlocking fit.

The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (e.g., hydroxypropylcellulose). In some embodiments, the synthetic polymers having a carboxyl group, may comprise poly(acrylic acid), poly(methacrylic acid), poly(vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyl-disulfide, maleimide, aldehyde, iodoacetamide or a combination thereof. In some embodiments, the adhesive material can comprise at least one of fibrin, a cyanoacrylate (e.g., N-butyl-2-cyanoacrylate, 2-octyl-cyanoacrylate, etc.), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site, cannula and/or expandable member. In some embodiments, to have the device adhere to the target tissue site, pressure is applied in a direction substantially perpendicular to a surgical incision.

Multi-component adhesives harden by mixing two or more components, which chemically react. This reaction causes polymers to cross-link into acrylics, urethanes, and/or epoxies. There are several commercial combinations of multi-component adhesives in use in industry. Some of these combinations are polyester resin-polyurethane resin, polyols-polyurethane resin, acrylic polymer-polyurethane resins, or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied (e.g., body heat), the components react and cross-link. This type of adhesive includes epoxies, urethanes, and/or polyimides. The adhesive can be a moisture curing adhesive that cures when it reacts with moisture present (e.g., bodily fluid) on the substrate surface or in the air. This type of adhesive includes cyanoacrylates or urethanes. The adhesive can have natural components, such as for example, vegetable matter, starch (dextrin), natural resins or components from animals, e.g., casein or animal glue. The adhesive can have synthetic components based on elastomers, thermoplastics, emulsions, and/or thermosets including epoxy, polyurethane, cyanoacrylate, or acrylic polymers.

In some embodiments, the interbody spinal implant may be joined together utilizing pins, rods, clips, or other fasteners to allow strong and easy coupling of component parts.

In some embodiments, the allograft material is configured to provide the most contact to tissue surfaces (e.g., the allograft material can be on the perimeter of the device, while the polymer material is situated in the interior of the device).

According to some embodiments, fusion may be facilitated or augmented by introducing or positioning various osteoinductive materials within the cavities in the expandable implant device. Such osteoinductive materials may be introduced before, during, or after insertion of the exemplary spinal implant, and may include (but are not necessarily limited to) autologous bone harvested from the patient receiving the implant device, bone allograft, bone xenograft, bone morphogenic protein, bone marrow aspirate (BMA) and/or bio-resorbable compositions. These materials are suitable for the manufacture of both the spinal implant and the bone insert.

The bone insert may comprise a biocompatible material. In one embodiment, the material is biopolymer such as PLA, PGA, PEG, or Polycaprolactone (PCL).

In one embodiment, the osteoinductive material can be added to the spinal implant, for example, at the filling hole or other areas of the implant. The osteoinductive material may comprise allograft tissue. Non-limiting examples of a bone graft material include demineralized bone matrix, or a bone composite. While allograft bone is a desirable alternative to autograft, it must be rigorously processed and terminally sterilized prior to implantation to remove the risk of disease transmission or an immunological response. This processing removes the osteogenic and osteoinductive properties of the allograft, leaving only an osteoconductive scaffold.

In one embodiment, to improve the osteoinductive properties, it is desirable to use demineralized bone matrix (DBM) as the osteoinductive material, due to its superior biological properties relative to undemineralized allograft bone, since the removal of minerals increases the osteoinductivity of the graft. Currently, there are a range of DBM products in clinical use.

Demineralized bone matrix (DBM) is demineralized allograft bone with osteoinductive activity. DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (e.g., glycerol or a polymer). DBM is mostly an osteoinductive product, but it lacks enough induction to be used on its own in challenging healing environments such as a posterolateral spine fusion.

According to some embodiments of the disclosure, the demineralized bone matrix may comprise demineralized bone matrix fibers and/or demineralized bone matrix chips. In some embodiments, the demineralized bone matrix may comprise demineralized bone matrix fibers and demineralized bone matrix chips in a 30:70 ratio.

The demineralized allograft bone material may be further modified such that the original chemical forces naturally present have been altered to attract and bind growth factors, other proteins and cells affecting osteogenesis, osteoconduction and osteoinduction. For example, a demineralized allograft bone material may be modified to provide an ionic gradient to produce a modified demineralized allograft bone material, such that implanting the modified demineralized allograft bone material results in enhanced ingrowth of host bone.

In one embodiment, an ionic force change agent may be applied to modify the demineralized allograft bone material. The demineralized allograft bone material may comprise, e.g., a demineralized bone matrix (DBM) comprising fibers, particles and any combination of thereof. According to another embodiment, a bone graft structure may be used which comprises a composite bone, which includes a bone powder, a polymer and a demineralized bone.

The ionic force change agent may be applied to the entire demineralized allograft bone material or to selected portions/surfaces thereof.

The ionic force change agent may be a binding agent, which modifies the demineralized allograft bone material or bone graft structure to bind molecules, such as, for example, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7 (OP-1), rhBMP-7, GDF-5, LIM mineralization protein, platelet derived growth factor (PDGF), transforming growth factor-ß (TGF-ß), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

If a cell culture is employed, the cells include but are not limited to mesenchymal stems cells, pluripotent stem cells, osteoprogenitor cells, osteoblasts, osteoclasts, and any bone marrow-derived cell lines.

In some embodiments, the ionic force change agent comprises at least one of enzymes, enzyme mixtures, pressure (e.g., isostatic pressure), chemicals, heat, sheer force, oxygen plasma, or a combination thereof. For example, the ionic force change agent may comprise an enzyme such as collagenase or pepsin, which can be administered for a sufficient period of time to partially digest at least a portion of the demineralized allograft bone material. Subsequently, the enzyme may be deactivated and/or removed.

Any enzyme or enzyme mixture may be contemplated, and treatment time durations may be altered in accordance with the enzyme(s) used. Some suitable enzymes that may degrade the DBM material include, but are not limited to, cysteine proteinases, matrix metalloproteinases, enzymes such as amylases, proteases, lipases, pectinases, cellulases, hemicellulases, pentosanases, xylanases, phytases or combinations thereof. Exemplary enzymes suitable to partially degrade and modify the DBM material, include but are not limited to, cathepsin L, cathepsin K, cathepsin B, collagenase, pepsin, plasminogen, elastase, stromelysin, plasminogen activators, or a combination thereof.

In some embodiments, the DBM material can be subjected to pressure to modify it. The simplest pressing technique is to apply pressure to the unconstrained DBM material. Examples include pressing the DBM material using a mortar and pestle, applying a rolling/pressing motion such as is generated by a rolling pin, or pressing the bone pieces between flat or curved plates. These flattening pressures cause the DBM material fibers to remain intact.

Another pressing technique involves mechanically pressing demineralized bone material, which can be constrained within a sealed chamber having a hole (or a small number of holes) in its floor or second plate. The separated fibers extrude through the holes with the hole diameter limiting the maximum diameter of the extruded fibers. This constrained technique results in fibers that are largely intact (as far as length is concerned).

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone particles can be carried out at from about 1,000 to about 40,000 psi, and preferably at from about 5,000 to about 20,000 psi.

Subsequent to the addition of the ionic force change agent, the practitioner may optionally administer an appropriate molecule or cell culture. Generally, the molecule or cell culture is applied within minutes, for example from about 1 to about 120 minutes before implantation into the patient.

One class of molecules suitable for one embodiment of the disclosure is growth factors. Growth factors suitable for use in the practice of the disclosure include, but are not limited to, bone morphogenic proteins, for example, BMP-2, rhBMP-2, BMP-4, rhBMP-4, BMP-6, rhBMP-6, BMP-7 (OP-1), rhBMP-7, GDF-5, and rhGDF-5. Bone morphogenic proteins have been shown to be excellent at growing bone and there are several products being tested. rhBMP-2 can also be used on a carrier for acute, open fractures of the tibial shaft. BMP-7 (OP-1) also enhances bone growth in a posterolateral fusion procedure.

Additionally, suitable growth factors include, without limitation, LIM mineralization protein, platelet derived growth factor (PDGF), transforming growth factor ß (TGF-ß), insulin-related growth factor-I (IGF-I), insulin-related growth factor-II (IGF-II), fibroblast growth factor (FGF), and beta-2-microglobulin (BDGF II).

Further, molecules, which do not have growth factor properties, may also be suitable for this disclosure. An example of such molecules is tartrate-resistant acid phosphatase.

In one embodiment, the demineralized allograft bone material is treated with a negatively-charged ionic force change agent to produce a negatively-charged demineralized allograft bone material. The negatively-charged demineralized allograft bone material attracts a positively charged molecule having a pI from about 8 to about 10. Examples of positively charged molecules having a pI from about 8 to about 10 include but are not limited to, rhBMP-2 and rhBMP-6.

In another embodiment, the demineralized allograft bone material is treated with a positively-charged ionic force change agent such that the positively-charged demineralized allograft bone material attracts a molecule with a slightly negative charge, for example a charge of pI about 5 to about 7. Examples of molecules having a slightly negative charge include rhBMP-4.

In yet another embodiment, the demineralized allograft bone material is treated with a positively-charged ionic force change agent to produce a positively-charged demineralized allograft bone material such that cells, in particular cell cultures having a negative surface charge bind to the positively-charged demineralized allograft bone material.

Examples of cells which are suitable for use in the practice of the disclosure include but are not limited to mesenchymal stems cells, pluripotent stem cells, embryonic stem cells, osteoprogenitor cells and osteoblasts.

The mechanisms by which a demineralized allograft bone material may acquire ionic forces include, but are not limited to, ionization, ion adsorption and ion dissolution.

In one embodiment, the implant is modified to give it the selected charge by a one-to-one substitution of the calcium ion with lithium, sodium, potassium or cesium of hydroxyapatite.

In yet another aspect, treatments with gradient-affecting elements, such as elements present in hydroxyapatite, and human proteins are employed. Suitable gradient-affecting proteins are those present in the organic phase of human bone tissue. The gradient-affecting proteins derive molecule or cell attraction without the potential damaging effects on the implants, as may be the case with other chemical treatments. Usually this is accomplished through surface treatments such as, for example, plasma treatment to apply an electrostatic charge on bone.

The term "plasma" in this context is an ionized gas containing excited species such as ions, radicals, electrons and photons. The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces. Plasma treatment is an effective method to uniformly alter the surface properties of substrates having different or unique size, shape and geometry including, but not limited to, bone and bone composite materials.

Having been deposited in the disc space, the spinal implant of the present disclosure effects spinal fusion over time as the natural healing process integrates and binds the implant within the intervertebral space by allowing a bony bridge to form through the implant and between the adjacent vertebral bodies.

In some embodiments, an implant device of the present disclosure may be used to deliver substances such as surface demineralized bone chips, optionally of a predetermined particle size, demineralized bone fibers, optionally pressed, and/or allograft.

For embodiments where the substance is biologic, the substance may be autogenic, allogenic, xenogenic, or transgenic. However, it is contemplated that other suitable materials may be positioned in the implant device such as, for example, protein, nucleic acid, carbohydrate, lipids, collagen, allograft bone, autograft bone, cartilage stimulating substances, allograft cartilage, TCP, hydroxyapatite, biphasic calcium phosphate, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the implant device. A substance provided within the implant device may be homogenous, or generally a single substance, or may be heterogeneous, or a mixture of substances.

In some embodiments the substance delivered by the implant device may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, such as SEMA3, control vascular morphogenesis by inhibiting integrin function in the vascular system and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; anti-microbials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-ß); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment, the spinal implant comprises at least one hole, gap, or filling hole and it is contemplated that any combination or mixture of same or different substances may be placed and retained therein, and further, different substances may be placed within the same or different holes, gaps, or filling holes.

Sterilization

The spinal implant according to the present disclosure including its contents must be sterilizable. In various embodiments, one or more components of the implant device and/or its contents are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms; they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the spinal implant. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

E-beam sterilization may be used, for example, when the spinal implant has gel components, such as when the insert is in a gel form.

Other methods may also be used to sterilize the device and/or one or more components of the device and/or contents, including, but not limited to, gas sterilization, such as, for example, with ethylene oxide or steam sterilization.

Methods of Use

The spinal implant comprising the compressible insert can be used for fusing two adjacent vertebrae. In some embodiments, there is a method for fusing two adjacent vertebrae, the method comprising placing a spinal implant having at least two ends into an intervertebral space adjacent vertebrae in need of fusion, the spinal implant configured to receive an insert; placing the insert into the spinal implant and compressing the insert into a compressed state, wherein a height of the insert is the same or shorter than a height of the spinal implant, the insert comprising a first portion having a first surface and a compressible support adjacent to the first surface; and a second portion having a second surface and a second compressible support adjacent to the second surface.

The spinal implant and/or insert can receive bone material that can be added or loaded before, during or after implantation and can, in some embodiments, be added or loaded in the hole or gap or filling hole of the spinal implant.

Preloading may be done with any of the substances previously discussed including, for example, allograft such as DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate. In some embodiments, the substance for placement is used as the materials for making the insert. In some embodiments, the substances are filled around the insert. In some embodiments, the substances are filled in the first portion, middle portion, and/or second portion of the insert.

Any suitable method may be used for loading a substance in the implant device in the operating room or at the surgical site. For example, the substance may be spooned into the cavities or holes or gaps of the implant device, the substance may be placed in the implant device using forceps, the substance may be loaded into the implant device using a syringe (with or without a needle), or the substance may be inserted into the implant device in any other suitable manner. Specific embodiments for loading at the surgical site include, for example, vertebroplasty or interbody space filler.

For placement, the substance or substances may be provided in the implant device and the implant device placed in vivo. In one embodiment, the implant device is placed in vivo by placing the implant device in a catheter or tubular inserter and delivering the implant device with the catheter or tubular inserter. The implant device, with a substance provided therein, may be steerable such that it can be used with flexible introducer instruments, for example, minimally invasive spinal procedures. For example, the implant device may be introduced down a tubular retractor, cannula or scope, during PLIF, TLIF, ALIF, DLIF or other procedures.

Attachment mechanisms provided on the implant device may be used to couple the device to a site in vivo.

An implant device according to the present disclosure may be configured for use in any suitable application. In some embodiments, the implant device may be used in healing vertebral compression fractures, interbody fusion, minimally invasive procedures, posterolateral fusion, correction of adult or pediatric scoliosis and others. The implant device may be used in a minimally invasive procedure via placement through a small incision, via delivery through a tube, or other. The size and shape of the device may advantageously be designed in accordance with restrictions on delivery conditions.

An exemplary application for using an implant device as disclosed is fusion of the spine. In clinical use, the implant device and delivered substance may be used to bridge the gap between the transverse processes of adjacent or sequential vertebral bodies. The implant device may be used to bridge two or more spinal motion segments. The implant device surrounds the substance to be implanted and contains the substance to provide a focus for healing activity in the body.

In other applications, the implant device may be applied to transverse processes or spinous processes of vertebrae.

Generally, the implant device may be applied to a pre-existing defect, to a created channel, or to a modified defect. Thus, for example, a channel may be formed in a bone, or a pre-existing defect may be cut to form a channel, for receipt of the implant device. The implant device may be configured to match the channel or defect. In some embodiments, the configuration of the implant device may be chosen to match the channel. In other embodiments, the channel may be created, or the defect expanded or altered, to reflect a configuration of the implant device. The implant device may be placed in the defect or channel and, optionally, coupled using attachment mechanisms.

At the time just prior to when the implant device is to be placed in a defect site, optional materials, e.g., autograft bone marrow aspirate, autograft bone, preparations of selected autograft cells, autograft cells containing genes encoding bone promoting action, etc., can be combined with the implant device and/or with a substance provided in the implant device. The implant device can be implanted at the bone repair site, if desired, using any suitable affixation means, e.g., sutures, staples, bioadhesives, screws, pins, rivets, other fasteners and the like or it may be retained in place by the closing of the soft tissues around it.

Although the disclosure has been described with reference to some embodiments, persons skilled in the art will recognize that changes may be made in form and detail without departing from the spirit and scope of the disclosure.

What is claimed is:

1. A spinal implant for positioning between adjacent vertebrae, the spinal implant comprising a first contact surface and a second contact surface, the first contact surface and the second contact surface configured to contact adjacent vertebrae; and a gap configured to receive an insert; the insert configured to have a compressible height such that in a compressed state, the height of the insert is shorter than a height of the spinal implant and in an expanded state, the height of the insert is configured to extend beyond the first contact surface and the second contact surface, the insert further having a first portion and a second portion, the first portion comprising a first surface and a compressible support adjacent to the first surface and the second portion having a second surface and a second compressible support adjacent to the second surface of the insert, wherein the insert further comprising a middle portion between the first portion and the second portion, the middle portion comprising a pillar extending across the height of the middle portion and a block.

2. The spinal implant according to claim 1, wherein (i) the insert is configured to impart a vertical compression to the spinal implant; or (ii) when the insert is disposed in the gap, the insert is viewable in the spinal implant.

3. The spinal implant according to claim 1, wherein the insert is compressible such that a highest point of the insert corresponds to a highest point of the spinal implant.

4. The spinal implant according to claim 1, wherein the insert is compressible such that a contour of the first surface of the insert corresponds to a contour of the first contact surface of the spinal implant.

5. The spinal implant according to claim 1, wherein the insert is an osteoconductive insert.

6. The spinal implant according claim 1, wherein the insert comprises shape-memory material.

7. The spinal implant according to claim 1, wherein the insert is monolithic.

8. The spinal implant according to claim 1, wherein the spinal implant and/or insert comprise grooves, recesses, projections, serrations or combinations thereof.

9. The spinal implant according to claim 8, wherein the serrations have shapes comprising triangular, pyramid, cone, spike, keel shapes or combinations thereof.

10. A spinal implant for transforaminal interbody fusion of lumbar vertebral column segments, the spinal implant comprising a main body having a first surface and a second surface situated opposite the first surface, the first surface and the second surface configured to contact vertebral column segments, the main body also having an inner perimeter, a filling hole, and an engagement part, the engagement part having a recess configured to allow a portion of a positioning instrument to position the spinal implant between vertebral column segments; and an insert disposed in the filling hole, the insert comprising a first portion having a first surface and a compressible support adjacent to the first surface; and a second portion having a second surface and a second compressible support adjacent to the second surface, wherein the insert further comprises a middle portion between the first portion and the second portion, the middle portion comprising a pillar extending across the height of the middle portion and a block.

11. The implant according to claim 10, wherein the implant comprises an elastic synthetic material.

12. The implant according to claim 11, wherein the implant comprises polyetheretherketone (PEEK).

13. The implant according to claim 10, wherein the implant includes X-ray markers situated on the main body.

14. The implant according to claim 10, wherein the middle portion comprises a side support extending across a height of the middle portion and contacting the inner perimeter of the implant.

15. The implant according to claim 10, wherein the block is solid without any through hole.

16. The implant according to claim 10, wherein the block comprises a through hole.

17. A method for fusing two adjacent vertebrae, the method comprising placing a spinal implant having at least two ends into an intervertebral space adjacent vertebrae in need of fusion, the spinal implant configured to receive an insert; placing the insert into the spinal implant and compressing the insert into a compressed state, wherein a height of the insert is the same or shorter than a height of the spinal implant, the insert comprising a first portion having a first surface and a compressible support adjacent to the first surface; and a second portion having a second surface and a second compressible support adjacent to the second surface, wherein the insert further comprises a middle portion between the first portion and the second portion, the middle portion comprising a pillar extending across the height of the middle portion and a block.

18. The method according to claim 17, wherein the insert further comprises bone graft materials.

19. The method according to claim 17, wherein the middle portion comprises projections extending transversely from the pillar.

* * * * *